US009782581B2

(12) United States Patent
Howard et al.

(10) Patent No.: US 9,782,581 B2
(45) Date of Patent: Oct. 10, 2017

(54) METHODS AND SYSTEMS FOR ELECTRICAL STIMULATION INCLUDING A SHIELDED SHEATH

(71) Applicant: Boston Scientific Neuromodulation Corporation, Valencia, CA (US)

(72) Inventors: Joshua Dale Howard, Winnetka, CA (US); G. Karl Steinke, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 118 days.

(21) Appl. No.: 14/748,071

(22) Filed: Jun. 23, 2015

(65) Prior Publication Data
US 2015/0374977 A1    Dec. 31, 2015

Related U.S. Application Data

(60) Provisional application No. 62/018,295, filed on Jun. 27, 2014.

(51) Int. Cl.
*A61N 1/05* (2006.01)
*A61N 1/08* (2006.01)

(52) U.S. Cl.
CPC .................. *A61N 1/08* (2013.01); *A61N 1/05* (2013.01); *A61N 1/0534* (2013.01); *A61N 1/0551* (2013.01); *A61N 2001/086* (2013.01)

(58) Field of Classification Search
CPC .......... A61N 1/08; A61N 1/05; A61N 1/0534; A61N 1/0551; A61N 2001/086

(Continued)

(56) References Cited

U.S. PATENT DOCUMENTS

| 5,131,388 A | 7/1992 | Pless et al. |
| 5,336,246 A | 8/1994 | Dantanarayana |

(Continued)

FOREIGN PATENT DOCUMENTS

WO    2010126943    11/2010

OTHER PUBLICATIONS

Rezai, A. R., et al., "Neurostimulation system used for deep brain stimulation (DBS): MR safety issues and implications of failing to follow guidelines." Investigative Radiology, 39:300-303; 2004.

(Continued)

*Primary Examiner* — Michael Carey
(74) *Attorney, Agent, or Firm* — Lowe Graham Jones PLLC; Bruce E. Black

(57) ABSTRACT

An electrical stimulation system includes an electrical stimulation lead with at least one lead body, electrodes disposed along the distal end portion of the lead body(ies), terminals disposed along the proximal end portion of the lead body(ies), and conductors electrically coupling the terminals to the electrodes. The electrical stimulation system also includes a lead extension coupleable to the electrical stimulation lead. The lead extension includes a connector for receiving the proximal end portion of the electrical stimulation lead. The electrical stimulation system further includes a sheath defining a sheath lumen to slidingly receive a portion of the electrical stimulation lead or a portion of the lead extension or a portion of both the electrical stimulation lead and the lead extension. The sheath includes a flexible sheath body and an elongate RF shield disposed within the sheath body and extending along the sheath.

20 Claims, 9 Drawing Sheets

(58) Field of Classification Search
USPC .................. 607/115, 116, 117, 119, 122, 139
See application file for complete search history.

(56) References Cited

U.S. PATENT DOCUMENTS

| | | | |
|---|---|---|---|
| 5,699,801 A | 12/1997 | Atalar et al. | |
| 5,825,608 A | 10/1998 | Duva et al. | |
| 5,928,145 A | 7/1999 | Ocali et al. | |
| 6,031,375 A | 2/2000 | Atalar et al. | |
| 6,181,969 B1 | 1/2001 | Gord | |
| 6,240,317 B1 | 5/2001 | Villaseca et al. | |
| 6,263,229 B1 | 7/2001 | Atalar et al. | |
| 6,394,956 B1 | 5/2002 | Chandrasekaran et al. | |
| 6,408,202 B1 | 6/2002 | Lima et al. | |
| 6,508,765 B2 | 1/2003 | Suorsa et al. | |
| 6,510,345 B1 | 1/2003 | Van Bentem | |
| 6,516,227 B1 | 2/2003 | Meadows et al. | |
| 6,549,800 B1 | 4/2003 | Atalar et al. | |
| 6,606,513 B2 | 8/2003 | Lardo et al. | |
| 6,609,029 B1 | 8/2003 | Mann et al. | |
| 6,609,032 B1 | 8/2003 | Woods et al. | |
| 6,628,980 B2 | 9/2003 | Atalar et al. | |
| 6,673,999 B1 | 1/2004 | Wang et al. | |
| 6,675,033 B1 | 1/2004 | Lardo et al. | |
| 6,701,176 B1 | 3/2004 | Halperin et al. | |
| 6,714,809 B2 | 3/2004 | Lee et al. | |
| 6,741,892 B1 | 5/2004 | Meadows et al. | |
| 6,824,515 B2 | 11/2004 | Suorsa et al. | |
| 6,898,454 B2 | 5/2005 | Atalar et al. | |
| 6,904,307 B2 | 6/2005 | Karmarkar et al. | |
| 7,015,393 B2 | 3/2006 | Weiner et al. | |
| 7,133,714 B2 | 11/2006 | Karmarkar et al. | |
| 7,194,294 B2 | 3/2007 | Panescu et al. | |
| 7,236,816 B2 | 6/2007 | Kumar et al. | |
| 7,244,150 B1 | 7/2007 | Brase et al. | |
| 7,412,276 B2 | 8/2008 | Halperin et al. | |
| 7,437,193 B2 | 10/2008 | Parramon et al. | |
| 7,551,953 B2 | 6/2009 | Lardo et al. | |
| 7,561,906 B2 | 7/2009 | Atalar et al. | |
| 7,599,729 B2 | 10/2009 | Atalar et al. | |
| 7,620,453 B1 | 11/2009 | Propato et al. | |
| 7,672,734 B2 | 3/2010 | Anderson et al. | |
| 7,761,165 B1 | 7/2010 | He et al. | |
| 7,778,682 B2 | 8/2010 | Kumar et al. | |
| 7,822,460 B2 | 10/2010 | Halperin et al. | |
| 7,822,484 B1 | 10/2010 | Zhao et al. | |
| 7,844,319 B2 | 11/2010 | Susil et al. | |
| 7,848,788 B2 | 12/2010 | Tulley et al. | |
| 7,949,395 B2 | 5/2011 | Kuzma | |
| 7,957,783 B2 | 6/2011 | Atalar et al. | |
| 7,974,706 B2 | 7/2011 | Moffitt et al. | |
| 8,055,351 B2 | 11/2011 | Atalar et al. | |
| 8,108,028 B2 | 1/2012 | Karmarkar | |
| 8,175,710 B2 | 5/2012 | He | |
| 8,224,450 B2 | 7/2012 | Brase | |
| 8,322,026 B2 | 12/2012 | McDonald | |
| 8,335,570 B2 | 12/2012 | McDonald | |
| 8,340,782 B2 | 12/2012 | McDonald et al. | |
| 8,364,278 B2 | 1/2013 | Pianca et al. | |
| 8,364,279 B2 | 1/2013 | McDonald et al. | |
| 8,380,277 B2 | 2/2013 | Atalar et al. | |
| 8,380,324 B2 | 2/2013 | McDonald et al. | |
| 8,433,421 B2 | 4/2013 | Atalar et al. | |
| 8,478,423 B2 | 7/2013 | McDonald et al. | |
| 8,509,876 B2 | 8/2013 | Karmarkar | |
| 8,649,842 B2 | 2/2014 | Atalar et al. | |
| 8,688,226 B2 | 4/2014 | Atalar et al. | |
| 2001/0014820 A1 | 8/2001 | Gielen et al. | |
| 2004/0181177 A1 | 9/2004 | Lee et al. | |
| 2005/0070972 A1 | 3/2005 | Wahlstrand et al. | |
| 2005/0222633 A1 | 10/2005 | Edvardsson | |
| 2007/0150036 A1 | 6/2007 | Anderson | |
| 2008/0039898 A1 | 2/2008 | Lim et al. | |
| 2008/0051854 A1 | 2/2008 | Bulkes et al. | |
| 2008/0243218 A1 | 10/2008 | Bottomley et al. | |
| 2008/0262584 A1 | 10/2008 | Bottomley et al. | |
| 2009/0149906 A1 | 6/2009 | Ameri et al. | |
| 2009/0234368 A1 | 9/2009 | Gore | |
| 2009/0259272 A1 | 10/2009 | Reddy et al. | |
| 2009/0270956 A1* | 10/2009 | Vase | A61N 1/05 607/116 |
| 2010/0057175 A1 | 3/2010 | McDonald et al. | |
| 2010/0318098 A1* | 12/2010 | Lund | A61B 17/06109 606/129 |
| 2011/0112612 A1 | 5/2011 | Rahman | |
| 2011/0137414 A1 | 6/2011 | Litzke et al. | |
| 2011/0144449 A1 | 6/2011 | Ortiz et al. | |
| 2011/0152999 A1 | 6/2011 | Hastings et al. | |
| 2011/0234155 A1 | 9/2011 | Chen et al. | |
| 2011/0257703 A1 | 10/2011 | Kerber et al. | |
| 2012/0016355 A1 | 1/2012 | George et al. | |
| 2012/0035616 A1 | 2/2012 | Olsen et al. | |
| 2012/0041528 A1 | 2/2012 | Mehdizadeh et al. | |
| 2012/0041529 A1* | 2/2012 | Olsen | A61N 1/05 607/116 |
| 2012/0123500 A1 | 5/2012 | Erickson | |
| 2012/0158072 A1 | 6/2012 | Venook et al. | |
| 2012/0191167 A1 | 7/2012 | McDonald et al. | |
| 2012/0221074 A1 | 8/2012 | Brase et al. | |
| 2014/0034377 A1* | 2/2014 | Vij | A61M 25/0045 174/377 |
| 2014/0058482 A1 | 2/2014 | Gupta et al. | |
| 2014/0135614 A1 | 5/2014 | Venook et al. | |
| 2014/0214130 A1 | 7/2014 | Lopez et al. | |
| 2015/0031975 A1 | 1/2015 | Atalar et al. | |
| 2015/0073506 A1 | 3/2015 | Gupta et al. | |

OTHER PUBLICATIONS

Nyenhuis, J. A., et al., "MRI and implanted medical devices: basic interactions with an emphasis on heating." IEEE Transactions on Device and Materials Reliability, 5:467-478; 2005.

* cited by examiner

METHODS AND SYSTEMS FOR ELECTRICAL STIMULATION INCLUDING A SHIELDED SHEATH

CROSS-REFERENCE TO RELATED APPLICATIONS

This application claims the benefit under 35 U.S.C. §119 (e) of U.S. Provisional Patent Application Ser. No. 62/018, 295, filed Jun. 27, 2014, which is incorporated herein by reference.

FIELD

The present invention is directed to the area of implantable electrical stimulation systems and methods of making and using the systems. The present invention is also directed to implantable electrical stimulation leads and a shielded sheath that receives the lead, as well as to methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation system including an electrical stimulation lead with at least one lead body having a distal end portion and a proximal end portion, electrodes disposed along the distal end portion of the at least one lead body, terminals disposed along the proximal end portion of the at least one lead body, and conductors electrically coupling the terminals to the electrodes. The electrical stimulation system also includes a first sheath defining a sheath lumen to slidingly receive a portion of the electrical stimulation lead. The first sheath includes a flexible sheath body and an elongate RF shield disposed within the sheath body and extending along the first sheath.

In at least some embodiments, the system also includes a control module coupleable to the electrical stimulation lead. In at least some embodiments, the system also includes a lead extension coupleable to the electrical stimulation lead, the lead extension having a connector for receiving the proximal end portion of the electrical stimulation lead, the connector having a proximal end and a distal end, the connector including a connector housing defining a port at the distal end of the connector, the port configured and arranged for receiving the proximal end of the lead body of the electrical stimulation lead, and connector contacts disposed in the connector housing where the connector contacts are configured and arranged to couple to the terminals disposed on the proximal end of the lead body of the electrical stimulation lead. In at least some embodiments, the system also includes a second sheath defining a sheath lumen configured and arranged to slidingly receive a portion of the lead extension, the second sheath comprising a flexible sheath body and an elongate RF shield disposed within the sheath body and extending along the second sheath. In at least some embodiments, the first sheath is also configured and arranged to slidingly receive a portion of the lead extension including the connector.

Another embodiment is a method of implanting an electrical stimulation lead that includes providing the electrical stimulation system described above; implanting a distal portion of the electrical stimulation lead; forming a tunnel through patient tissue using a tunnel tool with the first sheath disposed over a portion of the tunneling tool; removing the tunneling tool from the patient tissue leaving the first sheath in the patient tissue; and sliding a portion of the electrical stimulation lead into the first sheath.

A further embodiment is an electrical stimulation system including an electrical stimulation lead with at least one lead body having a distal end portion and a proximal end portion, electrodes disposed along the distal end portion of the at least one lead body, terminals disposed along the proximal end portion of the at least one lead body, and conductors electrically coupling the terminals to the electrodes. The electrical stimulation system also includes a lead extension coupleable to the electrical stimulation lead. The lead extension includes a connector for receiving the proximal end portion of the electrical stimulation lead. The connector has a proximal end and a distal end and includes a connector housing defining a port at the distal end of the connector with the port configured and arranged for receiving the proximal end of the lead body of the electrical stimulation lead, and connector contacts disposed in the connector housing and configured and arranged to couple to at least one of the terminals disposed on the proximal end of the lead body of the electrical stimulation lead. The electrical stimulation system further includes a sheath defining a sheath lumen to slidingly receive a portion of the electrical stimulation lead or a portion of the lead extension or a portion of both the electrical stimulation lead and the lead extension. The sheath includes a flexible sheath body and an elongate RF shield disposed within the sheath body and extending along the sheath. In at least some embodiments, the system also includes a control module coupleable to the lead extension.

Yet another embodiment is a method of implanting an electrical stimulation lead that includes providing the electrical stimulation system described above; implanting a distal portion of the electrical stimulation lead; forming a tunnel through patient tissue using a tunnel tool with the sheath disposed over a portion of the tunneling tool; removing the tunneling tool from the patient tissue leaving the sheath in the patient tissue; sliding a portion of the lead extension into the sheath; and coupling the electrical stimulation lead to the lead extension.

Another embodiment is an electrical stimulation system including an implantable control module defining a port for receiving a proximal end of an electrical stimulation lead. The control module includes a power source and an electronic subassembly coupled to the power source to provide electrical stimulation current to the electrical stimulation lead for stimulation of patient tissue. The electrical stimulation system further includes a sheath defining a sheath lumen to slidingly receive a portion of the electrical stimulation lead. The sheath includes a flexible sheath body and an elongate RF shield disposed within the sheath body and extending along the first sheath. In at least some embodiments, the system further includes a lead extension coupleable to the control module.

Any of the sheaths described above can include a conductive braided tube or a conductive coiled tube as the RF shield.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads and a shielded sheath that receives the lead, as well as to methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036 (now U.S. Pat. No. 8,700,178), all of which are incorporated by reference.

Figure 1:
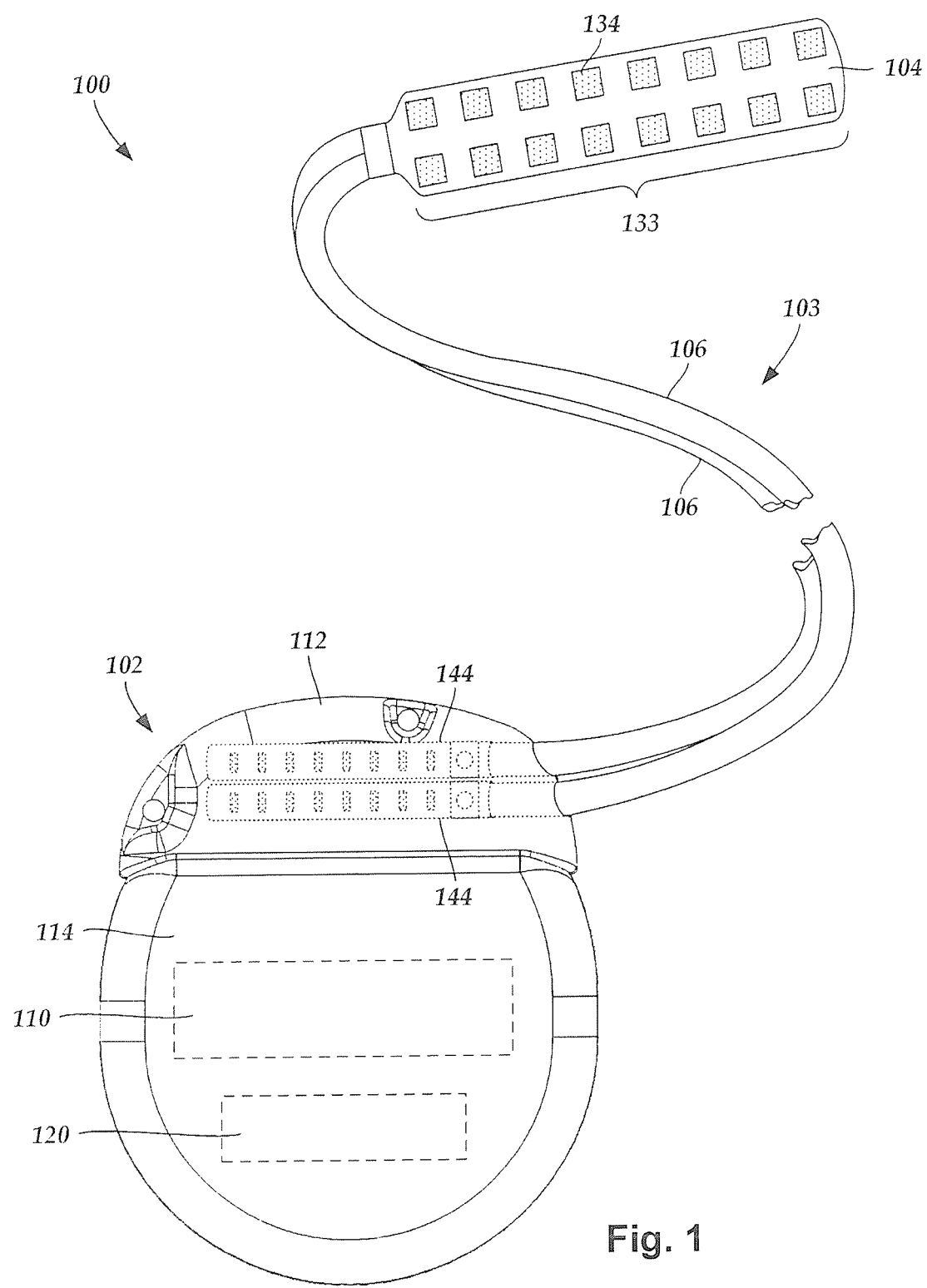
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
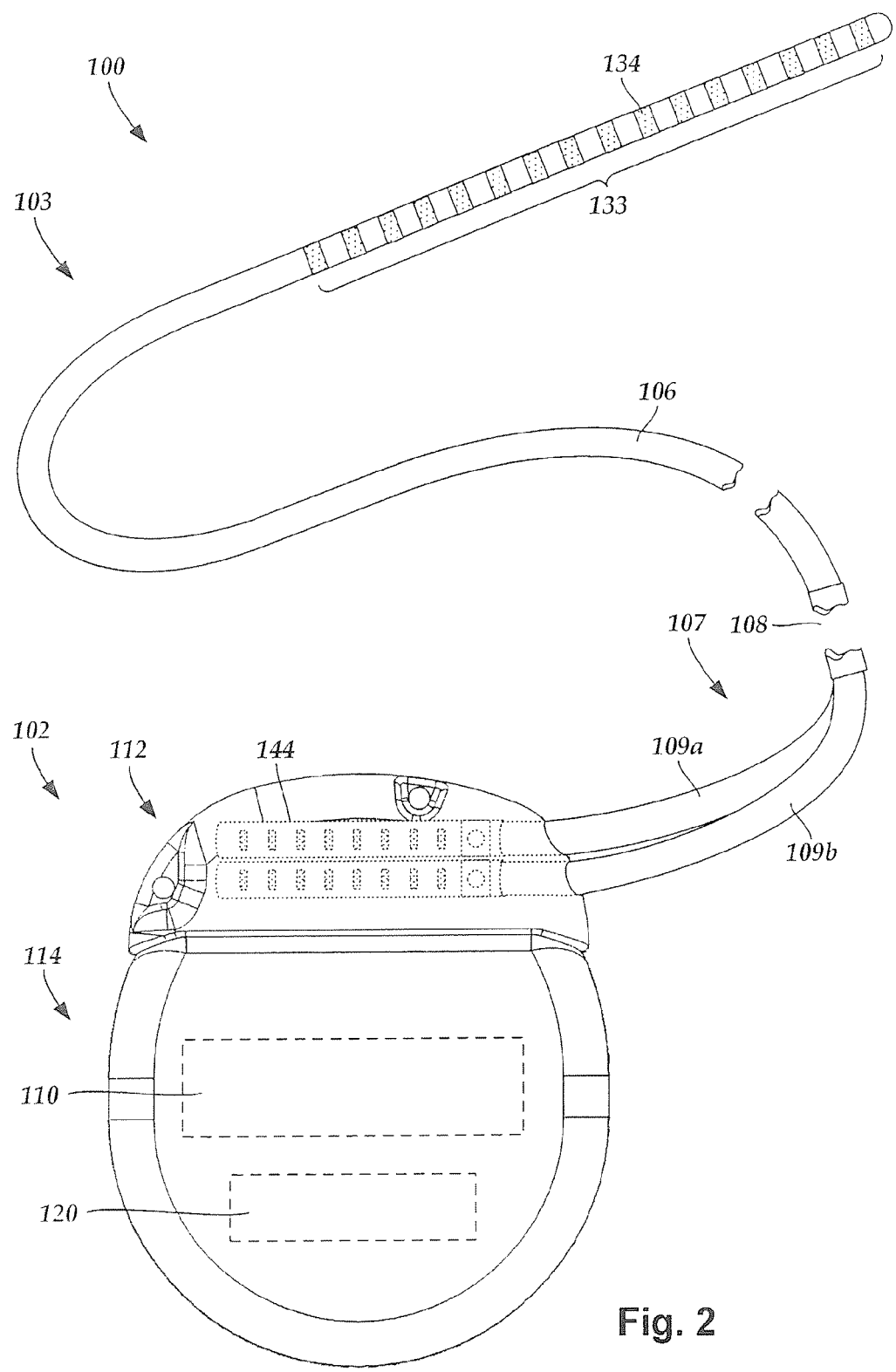
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together. It will be recognized that a paddle lead can also include more than one paddle body.

Figure 3A:
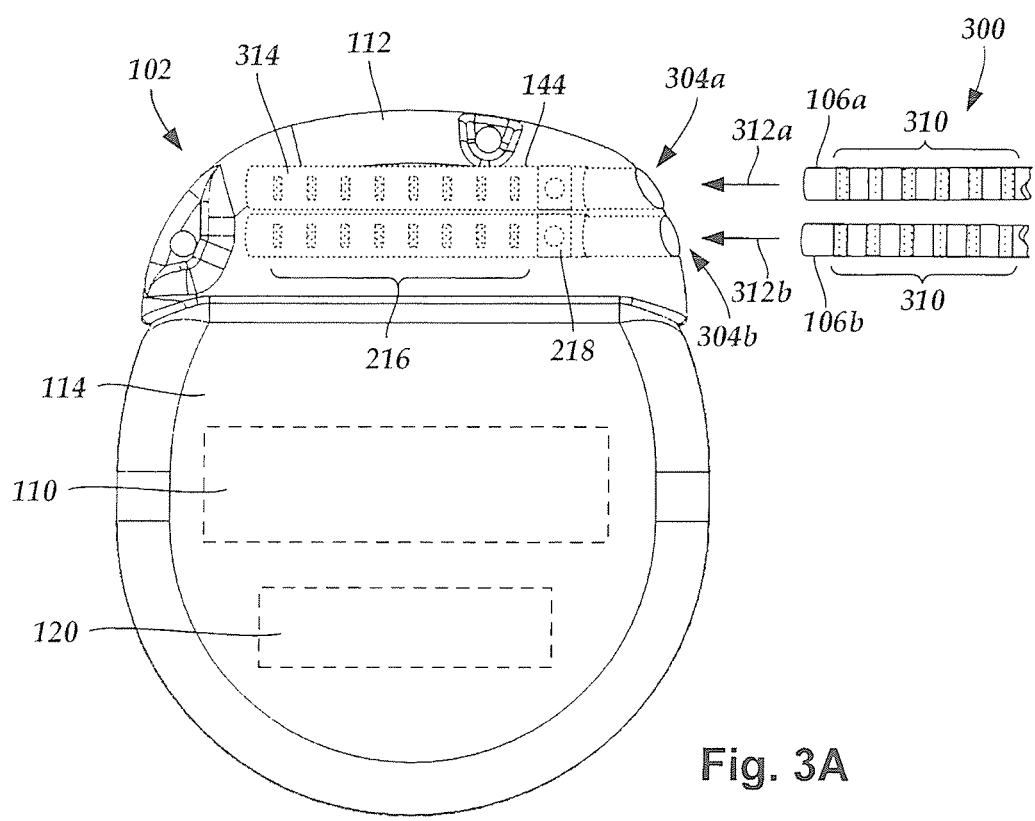
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
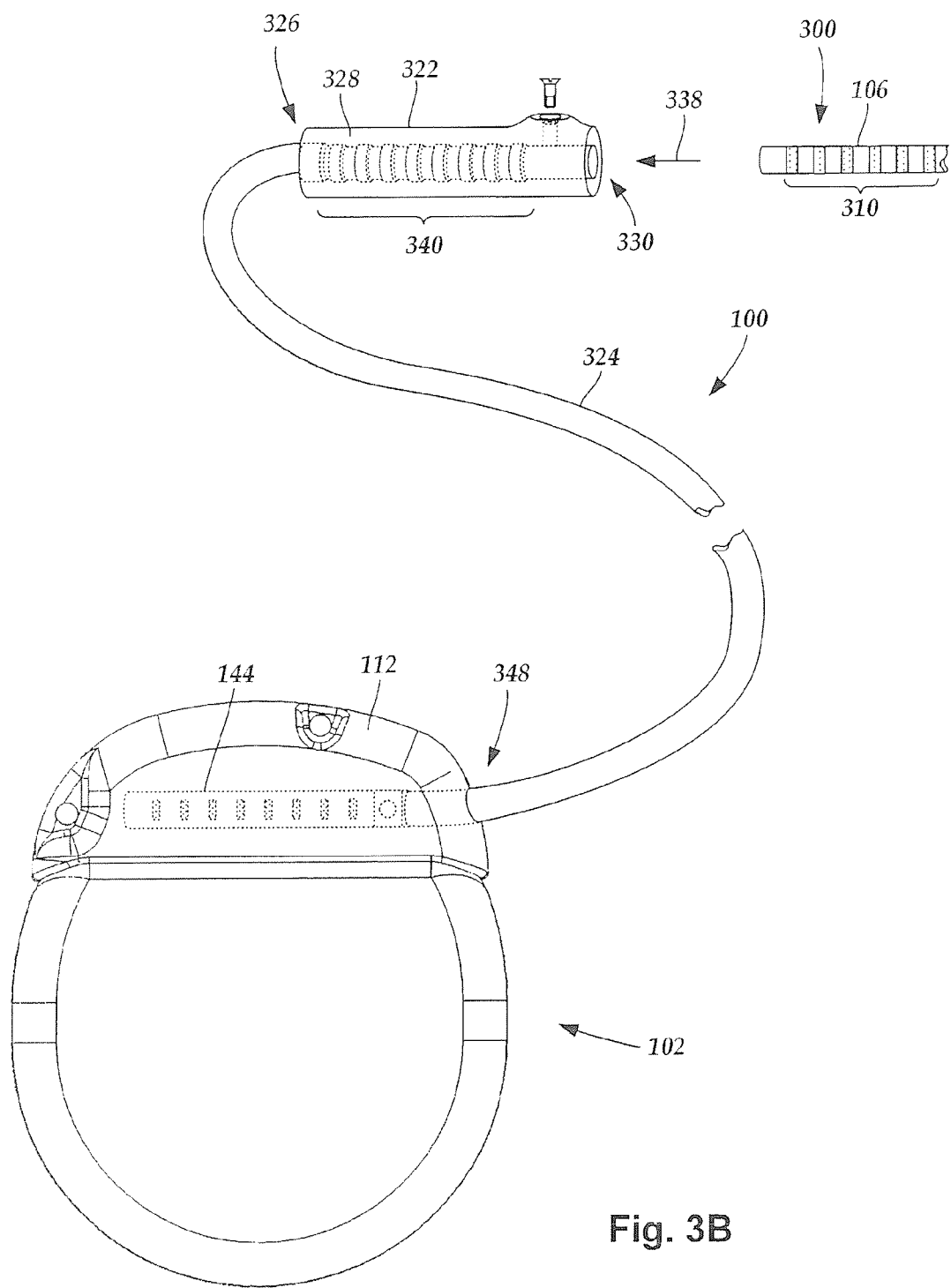
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4A:
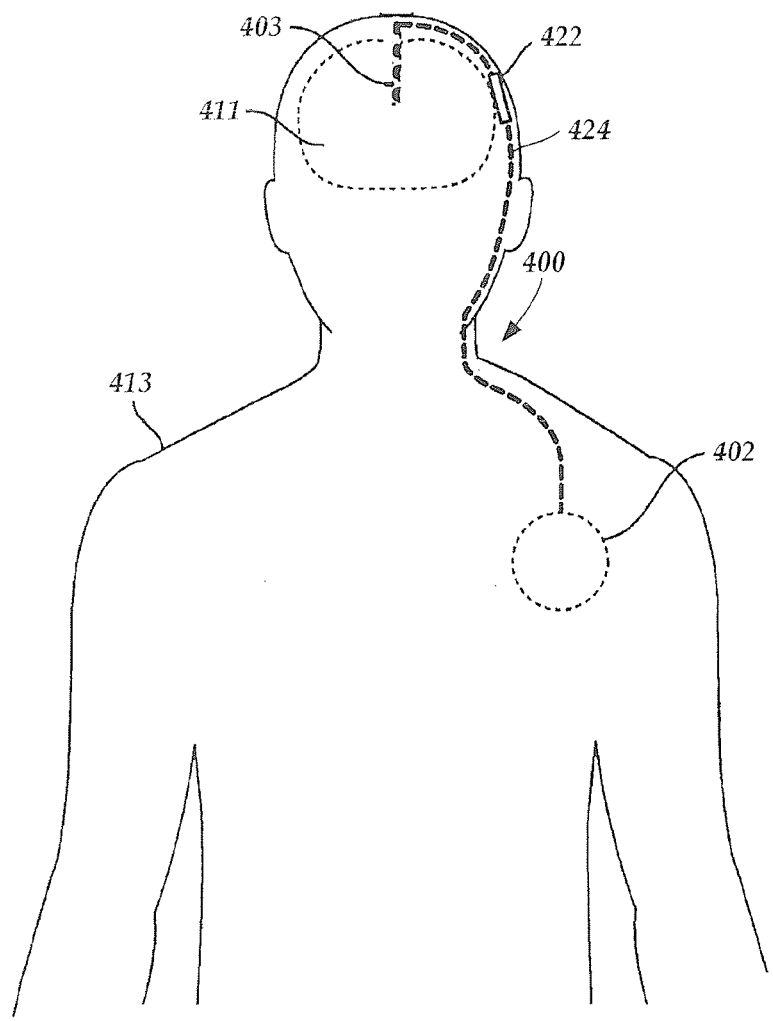
FIG. 4A is a schematic view of one embodiment of an electrical stimulation system implanted in a patient for deep brain stimulation, according to the invention.

FIG. 4A illustrates one example of an electrical stimulation system 400 for deep brain stimulation of the brain 411 of a patient 413. The electrical stimulation system includes a lead 403, a control module 402, and an optional extension 424 which includes a connector 422 that receives the proximal end of the lead (see, for example, FIG. 3B). It will be understood that the lead and other system components can be implanted elsewhere to achieve other types of stimulation including, but not limited to, spinal cord stimulation or stimulation of other body organs.

Figure 4B:
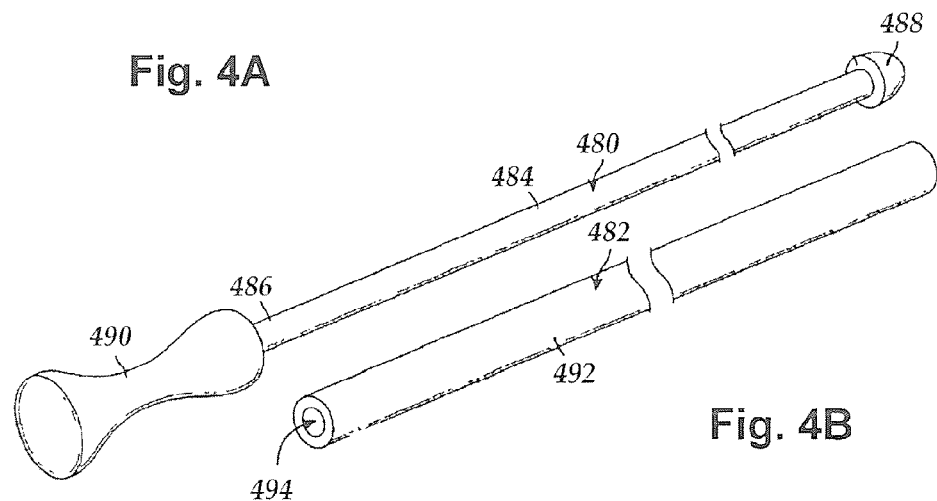
FIG. 4B is a schematic perspective view of one embodiment of a tunneling tool and sheath, according to the invention.

The distal end of the lead 403 is implanted at the stimulation site and the lead extends through a burr hole in the skull of the patient. The control module 402 is typically implanted elsewhere in the body, such as in the torso of the patient or in a subcutaneous pocket. A tunnel (for example, a subcutaneous tunnel) can be formed between the implantation sites of the lead and control module using a tunneling tool 480, as illustrated in FIG. 4B, over which a tunneling sheath 482 is disposed. After forming the tunnel, the tunneling tool 480 can be removed leaving the tunneling sheath 482 and a portion of the lead or a lead extension is slidingly inserted into and through the tunneling sheath.

In at least some embodiments, the tunneling tool 480 includes an elongated semi-rigid shaft 484 having a proximal end 486, a distal tip 488, and a handle 490 removably mounted to the proximal end of the shall. In at least some embodiments, the distal tip 488 can be an atraumatic blunt distal tip. The tunneling sheath 482 includes an elongated hollow body 492 and a lumen 494 extending through the body. In at least some embodiments, the body 492 is cylindrical. The lumen 494 of the tunneling sheath 482 is sized to separately receive the shaft 484 of the tunneling tool 480 and the lead body of the lead 403 or lead extension 424. In a tunneling procedure, the tunneling sheath 482 is typically placed around the tunneling tool 480 and remains in the tunnel when the tunneling tool is removed. The lead 403 or a lead extension 424 (or both) can then be inserted into the tunneling sheath 482 and slidingly passed through the sheath between the implantation sites of the control module 402 and distal end of the lead. In conventional procedures, the tunneling sheath 482 is removed after the lead or lead extension is in place. It will be recognized that separate tunneling procedures can be performed over different portions of the route between the implantation sites of the control module and the distal end of the lead.

Conventional electrical stimulation systems may be potentially unsafe for use with magnetic resonance imaging ("MRI") due to the effects of electromagnetic fields in an MRI environment. A common mechanism for causing the electrical interactions between the electrical stimulation system and RF irradiation is common-mode coupling of the applied electromagnetic fields that act as a series of distributed sources along elongated conductive structures, such as leads or lead extensions, or conductors within leads or lead extensions. Common-mode induced RF currents can reach amplitudes of greater than one ampere in MRI environments. Such currents can cause heating and potentially disruptive voltages within electronic circuits.

Some of the effects of RF irradiation may include, for example, inducing current in the lead or lead extension, causing undesired heating at the electrodes of the lead that may potentially cause tissue damage, undesired or unexpected operation of electronic components, or premature failure of electronic components. Additionally, when an electrical stimulation system is used within an MRI scanner environment, the electrical interactions between the electrical stimulation system and the MRI may cause distortions in images formed by the MRI system.

A sheath (or straw or tube), such as a tunneling sheath, can include an RF shield within the sheath and can remain implanted in the patient with the lead or lead extension disposed within the sheath to shield the lead or lead extension from external RF interference and prevent or reduce induction of current within the lead or lead extension by the external RF.

Figures 5A, 5B, 5C:
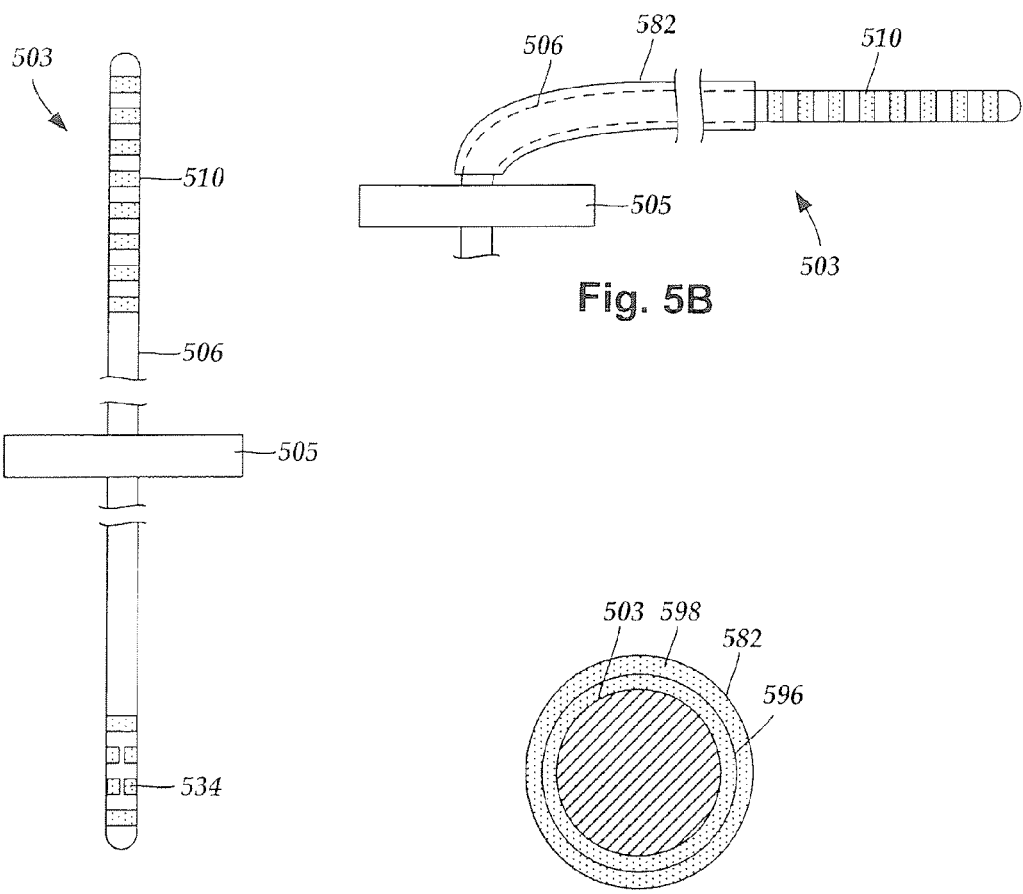
FIG. 5A is a schematic side view of one embodiment of an electrical stimulation lead implanted into a brain of a patient, according to the invention.
FIG. 5B is a schematic side view of the lead of FIG. 5A with a sheath over a portion of the lead, according to the invention.
FIG. 5C is a schematic cross-sectional view of the lead and sheath of FIG. 5B, according to the invention.

FIG. 5A illustrates one embodiment of a lead 503 with a lead body 506, terminals 510, and electrodes 534 implanted into the brain of a patient through a burr hole in the skull 505 of the patient. FIG. 5B illustrates the lead 503 with a tunneling sheath 582 disposed over a portion of the lead. A portion of the lead 503 is slidingly inserted into the tunneling sheath 582 after the tunneling sheath is in place within the tunnel. The particular termination points of the tunneling sheath 582 with respect to the lead 506 may vary from those illustrated in FIG. 5B, but, in at least some embodiments, the tunneling sheath 582 does not cover the terminals 510 of the lead 506 and does not extend past the burr hole in the skull 505 of the patient.

FIG. 5C is a cross-sectional view of the lead 503 and tunneling sheath 582. The tunneling sheath 582 includes a shield 596 embedded within a flexible sheath body 598. The flexible sheath body 598 can be formed of any suitable biocompatible polymeric material such as, for example, polyurethane, expanded polytetrafluoroethylene (ePTFE), or the like. The sheath body 598 is sufficiently thick to maintain structural integrity during the implantation procedure and, preferably, for at least one month, six months, one year, five years, ten years, or more after implantation. The sheath body 598 is preferably sufficiently thin so that the patient experiences little or no discomfort due to the implanted tunneling sheath 582.

The shield 596 of the tunneling sheath can have any suitable form including, but not limited to, a conductive braided tube or a conductive coiled tube. The shield 596 is made of a biocompatible conductive material, such as, for example, platinum, titanium, MP35N, 35N LT, 316L stainless steel, tantalum, or any other suitable metal or alloy. The shield 596 prevents or reduces the induction of current in the conductors of the lead 503 (or lead extension) disposed with the shield when exposed to RF irradiation. In at least some embodiments, the shield 596 can be designed to shield the lead 503 from RF at one or more specific frequencies, such as specific MRI frequencies (for example, 64 MHz, 128 MHz, or both) or any other frequency, frequency band, or set of frequencies or frequency bands. The shield 596 may extend along the entirety of the tunneling sheath 582 or may extend only partway (for example, at least 95%, 90%, 80%, 75%, 66%, 50%, or 25%) along the sheath. The shield may be aligned to some portion of the sheath (for example, centered, aligned to proximal end, aligned to distal end). The shield 596 can be electrically floating so that it has no electrical connection to the control module, lead, or lead extension or the shield may be grounded through the lead, lead extension, or control module.

Figure 6:
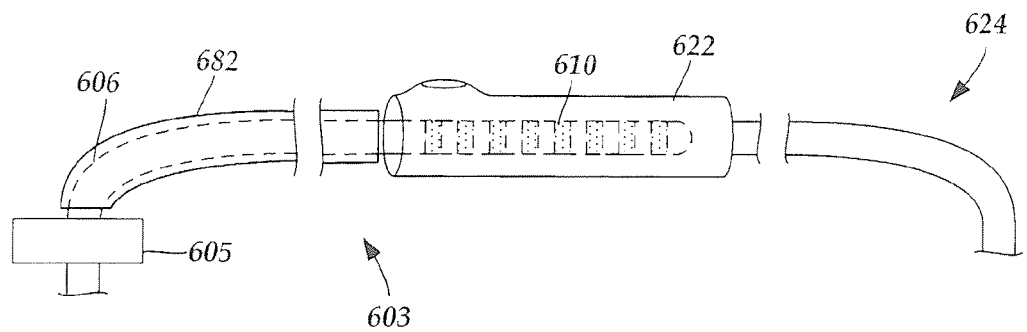
FIG. 6 is a schematic side view of one embodiment of an electrical stimulation lead implanted into a brain of a patient and a lead extension with a sheath over a portion of the lead, according to the invention.

FIG. 6 illustrates a lead 603 with a lead body 606 and terminals 610 implanted into the brain of a patient through a burr hole in the skull 605 of the patient. The lead 603 is coupled to a lead extension 624 using a connector 622. A tunneling sheath 682 disposed over a portion of the lead 603. The elements illustrated in the embodiment of FIG. 6, as well as design considerations for these elements, are the same as those described for similarly named elements in FIGS. 1-5B unless indicated otherwise.

Figure 7:
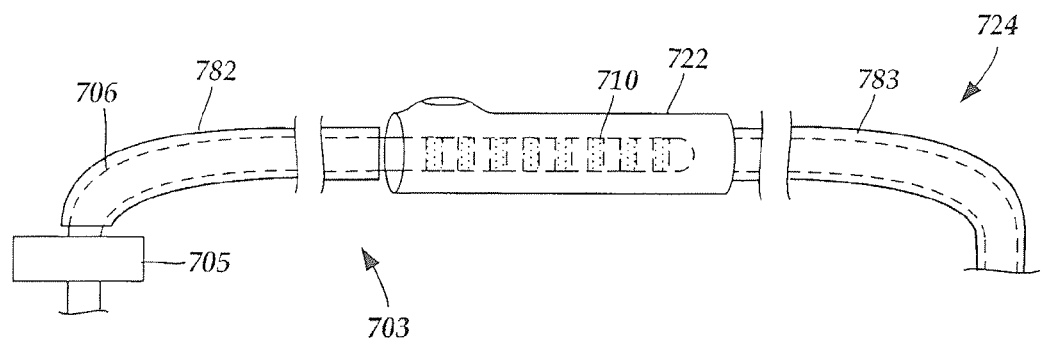
FIG. 7 is a schematic side view of one embodiment of an electrical stimulation lead implanted into a brain of a patient and a lead extension with sheaths over a portion of the lead and a portion of the lead extension, according to the invention.

FIG. 7 illustrates a lead 703 with a lead body 706 and terminals 710 implanted into the brain of a patient through a burr hole in the skull 705 of the patient. The lead 703 is coupled to a lead extension 724 using a connector 722. A first tunneling sheath 782 is disposed over a portion of the lead 703 and a second tunneling sheath 783 is disposed over a portion of the lead extension 724. The elements illustrated in the embodiment of FIG. 7, as well as design considerations for these elements, are the same as those described for similarly named elements in FIGS. 1-6 unless indicated otherwise. The second tunneling sheath 783 can be the same as the first tunneling sheath 782 (or any other tunneling sheath described herein.) The second tunneling sheath 783 can extend to any position along the lead extension 724. In some embodiments the second tunneling sheath 783 extends to or near the control module (see, for example, lead extension 424 and control module 402 in FIG. 4). In some embodiments, the second tunneling sheath 783 extends to or near the connector 722. In other embodiments, the tunneling sheath may terminate further away from the connector, control module, or both. Although FIG. 7 illustrates two tunneling sheaths, it will be recognized that one or more tunneling sheath can be used to cover the lead or the lead extension in this embodiment or any of the other embodiments described herein.

Figure 8:
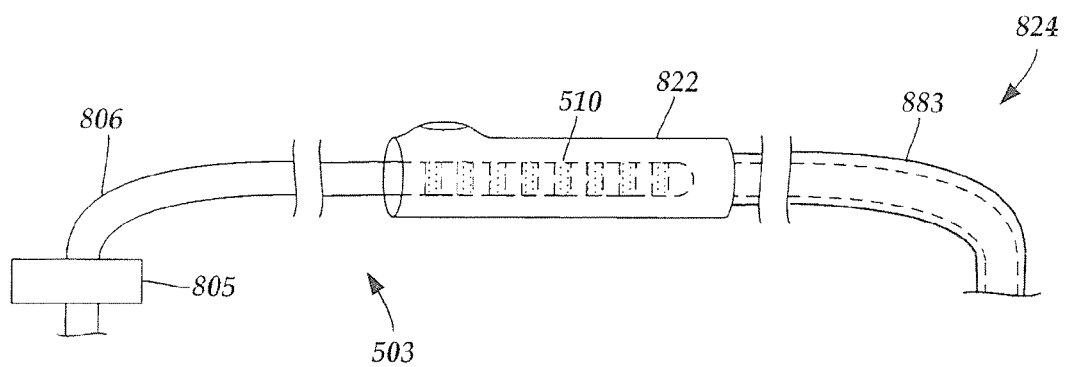
FIG. 8 is a schematic side view of one embodiment of an electrical stimulation lead implanted into a brain of a patient and a lead extension with a sheath over a portion of the lead extension, according to the invention.

FIG. 8 illustrates a lead 803 with a lead body 806 and terminals 810 implanted into the brain of a patient through a burr hole in the skull 805 of the patient. The lead 803 is coupled to a lead extension 824 using a connector 822. A tunneling sheath 883 is disposed over a portion of the lead extension 824. The elements illustrated in the embodiment of FIG. 8, as well as design considerations for these elements, are the same as those described for similarly named elements in FIGS. 1-7 unless indicated otherwise.

Figure 9:
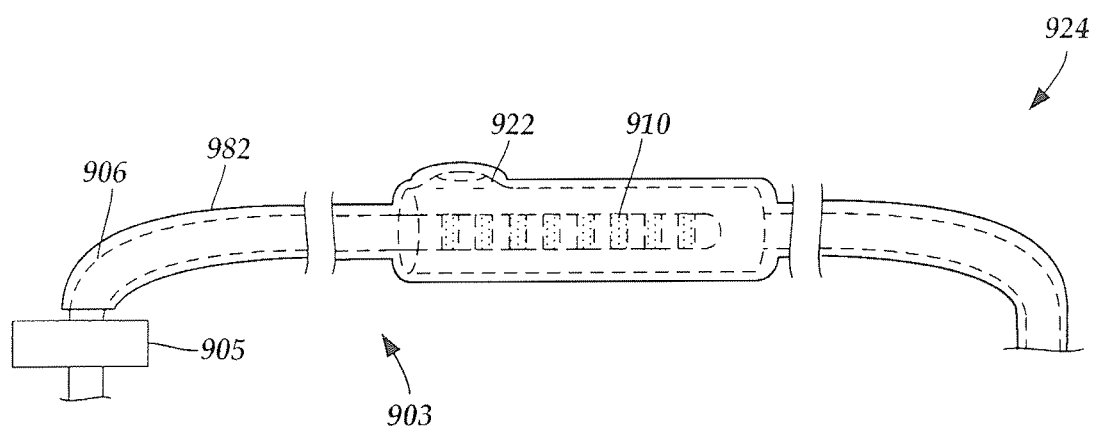
FIG. 9 is a schematic side view of one embodiment of an electrical stimulation lead implanted into a brain of a patient and a lead extension with a sheath over a portion of the lead and lead extension, according to the invention.

FIG. 9 illustrates a lead 903 with a lead body 906 and terminals 910 implanted into the brain of a patient through a burr hole in the skull 905 of the patient. The lead 903 is coupled to a lead extension 924 using a connector 922. A tunneling sheath 982 is disposed over a portion of the lead 903 and a portion of the lead extension 924 including the connector 922. The elements illustrated in the embodiment of FIG. 9, as well as design considerations for these elements, are the same as those described for similarly named elements in FIGS. 1-8 unless indicated otherwise. The tunneling sheath 982, including the shield 996, is formed so that it can stretch radially to slide over, and cover, the connector 922.

The tunnel sheath with RF shield is illustrated herein with respect to an electrical stimulation lead and electrical stimulation system for use in deep brain stimulation. It will be recognized, however, that a tunnel sheath with RF shield can be used with any other electrical stimulation lead or electrical stimulation system used to stimulate tissue in other parts of the body including, but not limited to, spinal cord stimulation and stimulation of other organs or tissues.

In some embodiments, the tunnel sheath remains in the body after implantation of the lead and closure of the surgical openings used to implant the lead and other portions of the electrical stimulation system. In other embodiments, the tunnel sheath may only temporarily remain in the tunnel and disposed around a portion of the lead or lead extension. For example, it may be desirable to obtain a MRI image during the implantation process and the tunnel sheath can be used to temporarily shield the lead or lead extension during the MRI procedure. The tunnel sheath may then be removed from the tunnel prior to the completion of the implantation process and closure of the surgical openings used to implant the lead and other portions of the electrical stimulation system.

A kit containing the tunneling sheath can also include one or more of the following, (in any combination); an electrical stimulation lead, a lead extension, or a control module.

One example of an implantation procedure includes implanting a distal portion of the electrical stimulation lead; forming a tunnel through patient tissue using a tunnel tool with the tunneling sheath disposed over a portion of the tunneling tool; removing the tunneling tool from the patient tissue leaving the tunneling sheath in the patient tissue; and sliding a portion of the electrical stimulation lead or lead extension (or both) into the tunneling sheath. This process can be repeated for multiple tunneling sheaths, if desired.

Although the sheath as described above is a tunneling sheath, it will be recognized that the sheath need not be used in a tunneling process or with a tunneling tool. Any of the sheaths described above can be slid over the lead or lead extension without first placing the sheath in a tunnel made using a tunneling tool.

Figure 10:
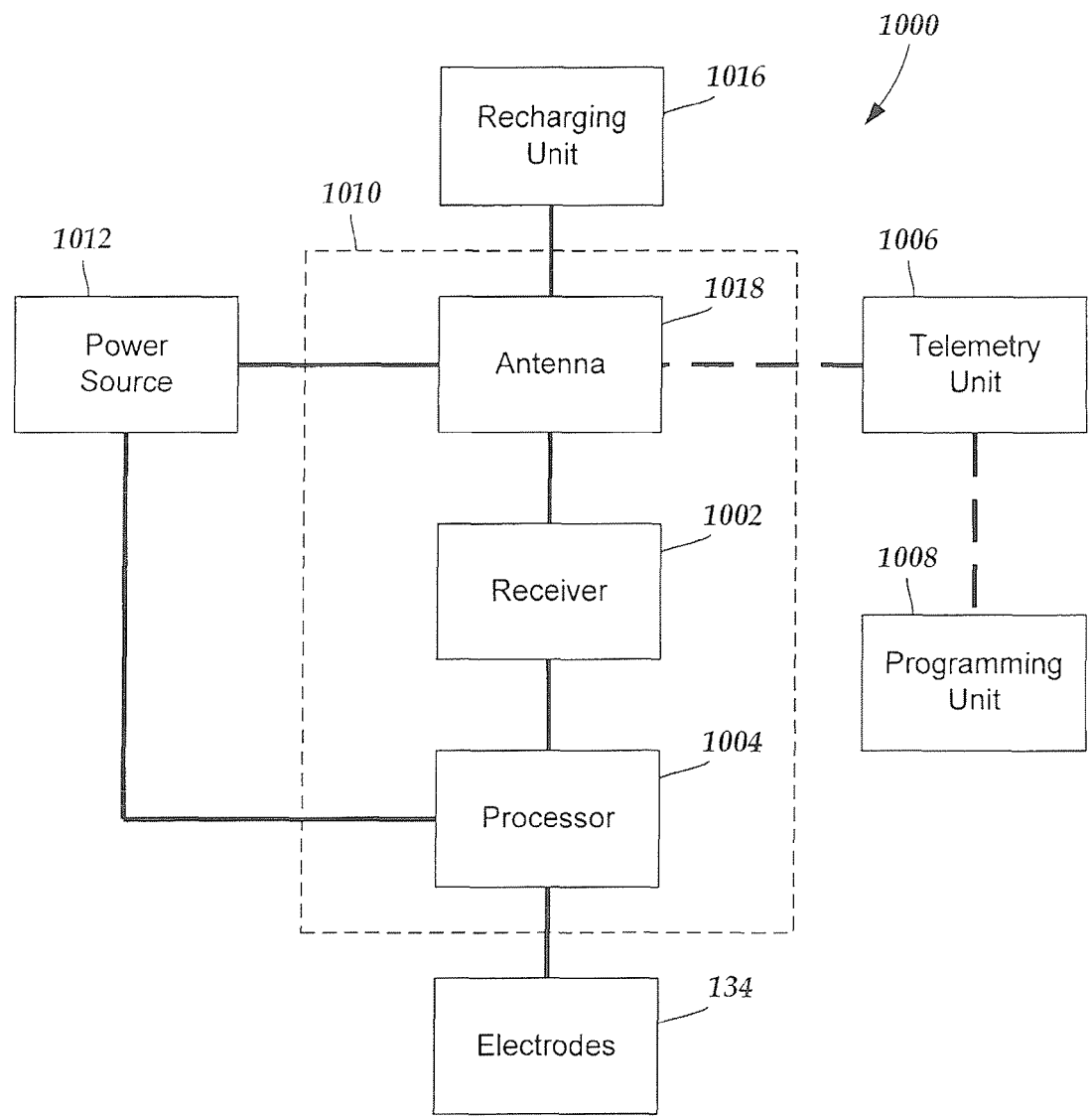
FIG. 10 is a schematic overview of one embodiment of components of a stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, a power source 1012, an antenna 1018, a receiver 1002, and a processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, or in addition, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 selects which electrode(s) are cathodes and which electrode(s) are anodes. In some embodiments, the processor 1004 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by the programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and the receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include the antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
an electrical stimulation lead comprising at least one lead body having a distal end portion and a proximal end portion, a plurality of electrodes disposed along the distal end portion of the at least one lead body, a plurality of terminals disposed along the proximal end portion of the at least one lead body, and a plurality of conductors electrically coupling the plurality of terminals to the plurality of electrodes; and
a first sheath defining a sheath lumen and configured and arranged to slide over and along the electrical stimulation lead to cover a selected portion of the electrical stimulation lead, the first sheath comprising a flexible sheath body and an elongate RF shield disposed within the sheath body and extending along the first sheath, wherein the first sheath is configured and arranged to radially stretch to cover a connector of a lead extension which has a diameter greater than a diameter of the electrical stimulation lead.

2. The electrical stimulation system of claim 1, further comprising a control module coupleable to the electrical stimulation lead.

3. The electrical stimulation system of claim 1, further comprising a lead extension coupleable to the electrical stimulation lead, the lead extension comprising a connector for receiving the proximal end portion of the at least one lead body of the electrical stimulation lead, the connector having a proximal end and a distal end, the connector comprising
- a connector housing defining a port at the distal end of the connector, the port configured and arranged for receiving the proximal end portion of the at least one lead body of the electrical stimulation lead, and
- a plurality of connector contacts disposed in the connector housing, the plurality of connector contacts configured and arranged to couple to at least one of the plurality of terminals disposed on the proximal end portion of the at least on lead body of the electrical stimulation lead.

4. The electrical stimulation system of claim 3, further comprising a second sheath defining a sheath lumen configured and arranged to slide over and along the electrical stimulation lead to cover a selected portion of the lead extension, the second sheath comprising a flexible second sheath body and a second elongate RF shield disposed within the second sheath body and extending along the second sheath.

5. The electrical stimulation system of claim 3, wherein the first sheath is also configured and arranged to slide over and cover a portion of the lead extension including the connector.

6. The electrical stimulation system of claim 1, wherein the RF shield is a conductive braided tube.

7. The electrical stimulation system of claim 1, wherein the RF shield is a conductive coiled tube.

8. An electrical stimulation system, comprising:
- an electrical stimulation lead comprising at least one lead body having a distal end portion and a proximal end portion, a plurality of electrodes disposed along the distal end portion of the at least one lead body, a plurality of terminals disposed along the proximal end portion of the at least one lead body, and a plurality of conductors electrically coupling the plurality of terminals to the plurality of electrodes;
- a lead extension coupleable to the electrical stimulation lead, the lead extension comprising a connector for receiving the proximal end portion of the electrical stimulation lead, the connector having a proximal end and a distal end, the connector comprising
  - a connector housing defining a port at the distal end of the connector, the port configured and arranged for receiving the proximal end portion of the at least one lead body of the electrical stimulation lead, and
  - a plurality of connector contacts disposed in the connector housing, the plurality of connector contacts configured and arranged to couple to at least one of the plurality of terminals disposed on the proximal end portion of the at least one lead body of the electrical stimulation lead; and
- a sheath defining a sheath lumen and configured and arranged to slide over and along the electrical stimulation lead or the lead extension to cover a selected portion of the electrical stimulation lead or a selected portion of the lead extension or a selected portion of both the electrical stimulation lead and the lead extension, the sheath comprising a flexible sheath body and an elongate RF shield disposed within the sheath body and extending along the sheath, wherein the sheath is configured and arranged to radially stretch to cover the connector of the lead extension which has a diameter greater than a diameter of the electrical stimulation lead.

9. The electrical stimulation system of claim 8, further comprising a control module coupleable to the lead extension.

10. The electrical stimulation system of claim 8, wherein the RF shield is a conductive braided tube.

11. The electrical stimulation system of claim 8, wherein the RF shield is a conductive coiled tube.

12. An electrical stimulation system, comprising:
- an implantable control module defining a port for receiving a proximal end of an electrical stimulation lead, the control module comprising a power source and an electronic subassembly coupled to the power source and configured and arranged to provide electrical stimulation current to the electrical stimulation lead for stimulation of patient tissue; and
- a sheath defining a sheath lumen and configured and arranged to slide over and along the electrical stimulation lead to cover a selected portion of the electrical stimulation lead, the sheath comprising a flexible sheath body and an elongate RF shield disposed within the sheath body and extending along the sheath, wherein the sheath is configured and arranged to radially stretch to cover a connector of a lead extension which has a diameter greater than a diameter of the electrical stimulation lead.

13. The electrical stimulation system of claim 12, wherein the RF shield is a conductive braided tube.

14. The electrical stimulation system of claim 12, wherein the RF shield is a conductive coiled tube.

15. A method of implanting an electrical stimulation lead, the method comprising:
- providing the electrical stimulation system of claim 1;
- implanting a distal portion of the electrical stimulation lead;
- forming a tunnel through patient tissue using a tunneling tool with the first sheath disposed over a portion of the tunneling tool;
- removing the tunneling tool from the patient tissue leaving the first sheath in the patient tissue; and
- sliding a portion of the electrical stimulation lead into the first sheath.

16. The method of claim 15, further comprising coupling the proximal end portion of the electrical stimulation lead to a control module leaving the first sheath within the patient tissue.

17. The method of claim 15, further comprising
- forming another tunnel through patient tissue using the tunneling tool with a second sheath disposed over a portion of the tunneling tool, the second sheath comprising a flexible second sheath body and a second elongate RF shield disposed within the second sheath body and extending along the second sheath;
- removing the tunneling tool from the patient tissue leaving the second sheath in the patient tissue;
- sliding a portion of a lead extension into the second sheath; and
- coupling the electrical stimulation lead to the lead extension.

18. The method of claim 15, further comprising coupling the electrical stimulation lead to a connector of a lead extension,
  wherein sliding a portion of the electrical stimulation lead into the first sheath comprises sliding the portion of the electrical stimulation lead and a portion of the lead extension, including the connector, into the first sheath.

19. A method of implanting an electrical stimulation lead, the method comprising:
providing the electrical stimulation system of claim 8;
implanting a distal portion of the electrical stimulation lead;
forming a tunnel through patient tissue using a tunneling tool with the sheath disposed over a portion of the tunneling tool;
removing the tunneling tool from the patient tissue leaving the sheath in the patient tissue;
sliding a portion of the lead extension into the sheath; and
coupling the electrical stimulation lead to the lead extension.

20. The method of claim 19, further comprising coupling a proximal end portion of the lead extension to a control module leaving the sheath within the patient tissue.

* * * * *